United States Patent [19]

Uda et al.

[11] Patent Number: 4,504,470

[45] Date of Patent: Mar. 12, 1985

[54] PHARMACEUTICAL PREPARATIONS CONTAINING TRH OR ITS ANALOGUE

[75] Inventors: Yoshiaki Uda; Takatsuka Yashiki, both of Takarazuka, Japan

[73] Assignee: Takeda Chemical Industries, Ltd., Osaka, Japan

[21] Appl. No.: 377,592

[22] Filed: May 12, 1982

[30] Foreign Application Priority Data

May 14, 1981 [JP] Japan .................................. 56/73293

[51] Int. Cl.[3] ...................... A61K 37/00; C07C 103/52
[52] U.S. Cl. .............................. 514/19; 260/112.5 TR
[58] Field of Search ................................. 424/177, 14; 260/112.5 TR

[56] References Cited

U.S. PATENT DOCUMENTS

| | | | |
|---|---|---|---|
| 3,959,247 | 5/1976 | Fujino et al. | 260/112.5 TR |
| 4,059,692 | 11/1977 | Takahashi et al. | 424/177 |
| 4,211,769 | 7/1980 | Okada et al. | 424/177 |
| 4,250,163 | 2/1981 | Nagai et al. | 424/14 |

Primary Examiner—Delbert R. Phillips
Attorney, Agent, or Firm—Wenderoth, Lind & Ponack

[57] ABSTRACT

A non-parenteral pharmaceutical preparation containing TRH, its salt, or its analogue is produced by employing the drug and a hydroxycarboxylic acid or polycarboxylic acid of 2 to 8 carbon atoms, and having the pH of the preparation adjusted to 2 to 6.

11 Claims, No Drawings

PHARMACEUTICAL PREPARATIONS CONTAINING TRH OR ITS ANALOGUE

This invention relates to a non-parenteral pharmaceutical preparation containing L-pyroglutamyl-L-histidyl-L-prolinamide (thyrotropin releasing hormone, hereinafter referred to briefly as TRH) or its analogue.

TRH is known to stimulate the release of thyroid stimulating hormone from the pituitary gland and, also, to act on the central nervous system, and there are also several known analogues thereof which have activities similar to those of TRH.

TRH and its analogues are all peptides, and because peptides generally are only sparingly lipophilic and are susceptible to enzymatic degradation in the gastrointestinal tract, these compounds are used almost exclusively as parenteral preparations. However, injections require the skilled hands of specialists and cause pain in recipients. Therefore, especially for repeated-dose administration, more convenient, easy-to-use dosage forms are desirable.

To overcome the above problem, the present inventors explored the possibility of developing non-parenteral dosage forms for TRH or its analogue. As a result, it was discovered that if a hydroxycarboxylic acid or polycarboxylic acid is incorporated in a preparation of TRH or its analogue, there can be expected an efficient absorption of the active compound in vivo even when it is administered by a non-parenteral route. This invention has been accomplished on the basis of the above finding.

This invention is therefore concerned with a non-parenteral pharmaceutical preparation containing TRH, its salt or its analogue and a hydroxycarboxylic acid or polycarboxylic acid of 2 to 8 carbon atoms, or tropic acid and having its pH adjusted to 2 to 6, and with a method for producing a non-parenterally administered drug form which comprises using a therapeutically effective dosage amount of L-pyroglutamyl-L-histidyl-L-prolinamide, its salt or its analogue capable of being absorbed into the blood stream and an adjuvant of hydroxycarboxylic acid or polycarboxylic acid of 2 to 8 carbon atoms, or tropic acid, said adjuvant being present in said drug form in a sufficient amount to be effective in enhancing said absorption ratio, and wherein the pH of said drug form is adjusted to 2 to 6.

TRH, which is employed in accordance with this invention, has the following structure:

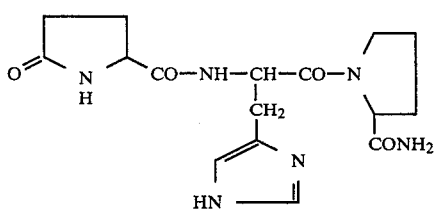

(I)

Salts of TRH include those with various acids (e.g. tartaric acid, oxalic acid, fumaric acid, citric acid, malic acid, acetic acid, lactic acid, oleic acid, palmitic acid, etc.) and is preferably the tartrate (U.S. Pat. No. 3,957,247, Japanese Patent Application Laid-open No. 121273/1975).

Analogues of TRH include peptides of the following formula:

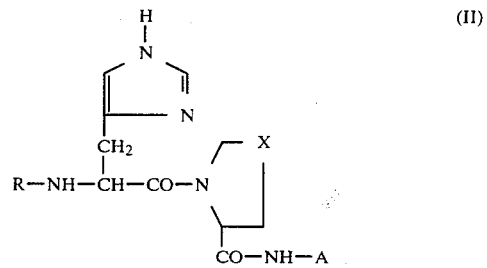

(II)

[A is H, alkyl, aralkyl, alkoxyalkyl, hydroxyalkyl or alkoxy; R is

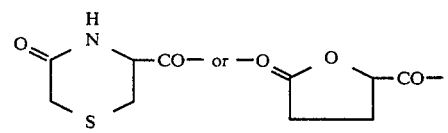

and when A is other than H, may also be

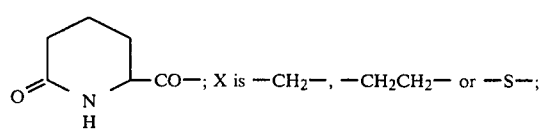

$-CO-$; X is $-CH_2-$, $-CH_2CH_2-$ or $-S-$;

R and each of the other constituent amino acid residues may have L- or D-configuration or be racemic] and salts thereof (Japanese Patent Application Laid-open No. 116465/1977; U.S. Pat. No. 4,100,152).

In said formula (II), the alkyl represented by A preferably contains 1 to 10 carbon atoms and to straight-chained or branched, and may for example be methyl, ethyl, propyl, i-propyl, butyl, sec-butyl, tert-butyl, i-butyl, amyl, hexyl, octyl, nonyl or decyl. The aralkyl represented by A is preferably one having the formula:

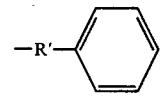

wherein R' is alkylene. The alkylene may for example be methylene, ethylene, 1,3-trimethylene ($-CH_2CH_2CH_2-$), propylene

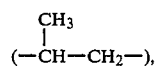

tetramethylene ($-CH_2CH_2CH_2CH_2-$) or 2-methyltrimethylene

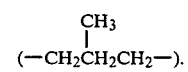

The alkoxyalkyl represented by A preferably contains up to 9 carbon atoms and is straight-chained or branched and may for example be methoxymethyl, methoxyethyl, propoxypropyl, butoxybutyl or methoxyoctyl. The alkoxy represented by A preferably contains up to 9 carbon atoms and is straight-chained or branched, and may for example be methoxy, ethoxy, propoxy, i-propoxy, butoxy, sec-butoxy, tert-butoxy, i-butoxy, pentyloxy, hexyloxy, octyloxy, nonyloxy or decyloxy. The hydroxyalkyl represented by A preferably contains up to 9 carbon atoms, and may for example be the same alkyl represented by A which is substituted by hydroxy on an optional position.

Among the compounds represented by the formula (II), γ-butyrolactone-γ-carbonyl-L-histidyl-L-prolinamide represented by the formula:

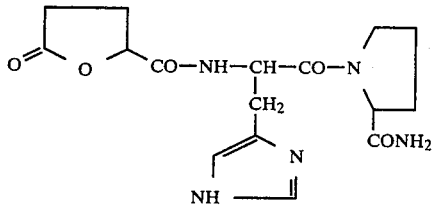

is preferable. In this specification, the compound is referred to briefly as "DN-1417".

The TRH analogue also includes tri-peptides of the general formula:

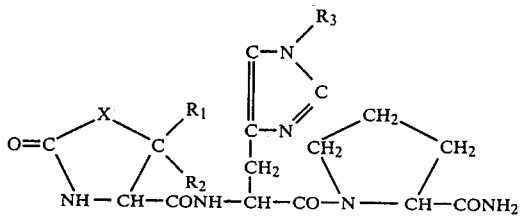

[X is O or S; $R_1$, $R_2$ and $R_3$ each is H or lower alkyl] and salts thereof (U.S. Pat. No. 3,912,705, Japanese Patent Application Laid-open No. 108075/1974); peptides of the formula $M_1$—$M_2$—$M_3$—E [(a) $M_1$ is selected from the class consisting of kio, kpc and pca, (b) $M_2$ is selected from the class consisting of his, $N^{3im}$-lower alkyl-his and $N^{3im}$-$(CH_2)_b$—COOH-his (where b is an integer of 1 to 4), (c) $M_3$ is selected from the class consisting of L-pip, L-pro and L-tca and (d) E is selected from the class consisting of —$NH_2$ and —OR (where R is $C_{1-10}$ alkyl); provided, however, that (i) when E is —$NH_2$, pca and L-pro do not occur concurrently in the tripeptide and (ii) when E is —OR, his and L-pro do not occur concurrently in the tripeptide] and salts thereof [in the above formula, kic is 2-ketoimidazolidine; kpc is 2-ketopiperidine-6-carboxylic acid; pca is pyroglutamic acid; his is histidine; L-pip is L-2-piperidinecarboxylic acid; pro is proline; and tca is thiazolidine-5-carboxylic acid] (U.S. Pat. No. 3,959,248, Japanese Patent Application Laid-open No. 154247/1975); and compounds of the formula:

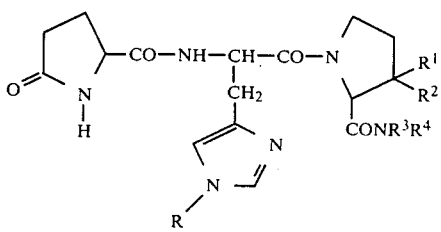

[R is H or $C_{1-3}$ alkyl; $R^1$ is $C_{1-3}$ alkyl or alkoxy; $R^2$ is H or $C_{1-3}$ alkyl or alkoxy; $R^3$ is H, $C_{1-6}$ alkyl or $C_{3-6}$ cycloalkyl; and $R^4$ is H or $C_{1-6}$ alkyl] and salts thereof (U.S. Pat. No. 4,060,603, Japanese Patent Application Laid-open No. 115272/1976).

The hydroxycarboxylic acid of 2 to 8 carbon atoms which is employed in accordance with this invention is exemplified by lactic acid, gluconic acid, malic acid, tartaric acid, citric acid, salicylic acid, mandelic acid, etc., and mandelic acid is preferable.

The polycarboxylic acid of 2 to 8 carbon atoms is exemplified by oxalic acid, fumaric acid, maleic acid, malonic acid, succinic acid, glutaric acid, etc., and succinic acid is preferable.

Tropic acid is also preferably used in this invention.

The addition level of said hydroxycarboxylic acid or polycarboxylic acid, based on the total weight of the composition, is at least about 0.1 weight percent, preferably at least about 1 weight % and, for still better results, at least about 3 weight %. The upper limit is about 50 weight %, preferably about 30 weight % and, for still better results, about 20 weight %.

The above-mentioned hydroxycarboxylic acid or polycarboxylic acid may be added in the form of a buffer solution. Examples of the buffer solution include Sörensen buffer [Ergebniss der Physiologie 12, 393(1912)], Michaelis buffer [Die Wasserstoffionenkonzentration p. 186(1914)], Kolthoff buffer [Biochemische Zeitschrift 179, 410(1926)], McIlvaine buffer [Journal of Biological Chemistry 49, 183(1921)] and so on.

When said carboxylic acid is added in the form of a buffer solution, the amount of the acid itself should be within the above-mentioned range.

The term "non-parenteral pharmaceutical preparation" is used herein to denote any of rectal dosage forms (e.g. suppositories, rectal capsules, infusions, etc.), nasal dosage forms (e.g. liquids, jellies, ointments, aerosols, inhalants, etc.), oral cavity dosage forms (e.g. tablets, buccals, troches, etc.) and oral dosage forms (e.g. tablets, capsules, pills, granules, granulets, powders, liquids, syrups, etc.).

Production of the non-parenteral pharmaceutical preparations according to this invention is conducted by an established procedure for producing non-parenteral preparations.

Thus, a preparation for rectal administration can be produced by adding said hydroxycarboxylic acid or polycarboxylic acid and TRH, its salt or its analogue to an oleaginous or aqueous basis, warming the mixture to a suitable temperature to dissolve or disperse them, pouring the resulting solution or dispersion into a mold, and cooling it, by way of example, all in the per se conventional manner.

When, for instance, an aqueous basis is used in the production of a rectal preparation, the desired preparation can be obtained by dissolving or dispersing said hydroxycarboxylic acid or polycarboxylic acid and THR, its salt or analogue evenly in the aqueous basis, pouring the solution or dispersion into a mold and cooling the same. Examples of said aqueous suppository bases include polyethylene glycol, glycero-gelatin, etc., and the preferred degree of polymerization of said polyethylene glycol is not less than 100, e.g. 200, 300, 400, 1000, 4000 and 6000. Such aqueous bases may be used alone or in admixture, and may also contain additives such as methylcellulose, carboxymethylcellulose, etc.

When an oleaginous basis is used in the production of a rectal preparation, the desired preparation can be obtained by dissolving or dispersing said hydroxycarboxylic acid or polycarboxylic acid in a fused mass of said oleaginous basis, then adding TRH, its salt or its analogue and dispersing the mixture evenly under appropriate heating and stirring or molding it. Alternatively, such a preparation may be produced by dispersing said hydroxycarboxylic acid or polycarboxylic acid in the oleaginous basis, dispersing an aqueous solution of TRH, its salt or its analogue, and molding the composition. Thus, these and other per se conventional procedures can be utilized to produce the desired preparation.

The above-mentioned oleaginous basis is exemplified by various oils and fats such as sesame oil, olive oil, corn oil, soybean oil, cotton-seed oil, peanut oil, castor oil, cacao butter, laurin fat, beef fat, lard, wool fat, squalene, etc.; and hydrogenolysis or fatty acid exchange reaction products thereof; mineral oils such as vaseline, paraffin, isopar, silicone oil, etc; glycerin esters of $C_{6-30}$ fatty acids, especially higher fatty acid esters such as glycerin palmitate, glycerin laurate, glycerin stearate, glycerin myristate, etc.; $C_{6-30}$ fatty acid esters of $C_{2-8}$ alcohols, especially waxes such as isopropyl myristate, butyl stearate, diisopropyl adipate, diethyl sebacate, etc.; and higher fatty acids containing 6 to 30 carbon atoms such as stearic acid, oleic acid, etc. These oils, fats and fatty acids may be used alone or in admixture. For the production of oleaginous suppositories, cacao butter, laurin fat, fatty acid exchange oil (e.g. mono-, di- and tri-glycerides of higher fatty acids such as palmitic acid, stearic acid, etc.), etc. are especially desirable.

For the production of nasal dosage forms, the above-mentioned various components are admixed in an optional order according to the established pharmaceutical procedure. For example, an aqueous liquid for nasal administration can be prepared by dissolving, suspending or emulsifying TRH, its salt or its analogue and said hydroxycarboxylic acid or polycarboxylic acid in water, a buffer solution or an aqueous solution. An aqueous gel for nasal administration, for instance, can be produced in the following manner. First, the hydroxycarboxylic acid or polycarboxylic acid is dissolved in water and, if necessary, a pH adjusting agent, a preservative, etc. are added to the aqueous solution. This solution is divided into halves, and a gel basis is dissolved or dispersed in one half, followed by heating at a suitable temperature or cooling to give a stable gel. TRH, its salt or its analogue is dissolved in the other half of said solution. The two solutions are evenly admixed to provide an aqueous gel.

Examples of the aqueous gel basis include natural gums (e.g. gum tragacanth, gum acasia, gum karaya, island moss, gum guaiac, gum xanthane, locust bean gum, etc.), cellulose derivatives (e.g. methylcellulose, carboxymethylcellulose, etc.), acrylic acid polymers (polyacrylic acid, polymethacrylic acid, etc.), vinyl polymers (e.g. polyvinyl pyrrolidone, polyvinyl alcohol, polyvinyl methyl ether, carboxypolymethylene, etc.), synthetic polysaccharides (e.g. polysucrose, polyglucose, polylactose, etc.), starch, dextrin, pectin, sodium alginate, etc. These bases may be used in the form of appropriate mixtures of two or more species.

Oil preparations for nasal administration can also be produced by dissolving, suspending or emulsifying TRH, its salt or its analogue and said hydroxycarboxylic acid or polycarboxylic acid in an oleaginous basis. As examples of said oleaginous basis, there may be mentioned oils and fats such as sesame oil, olive oil, corn oil, soybean oil, cotton-seed oil, peanut oil, etc.; mineral oils such as vaseline, paraffin, isopar, silicone oil, etc.; glycerin esters of $C_{6-30}$ fatty acids, especially higher fatty acid esters such as glycerin palmitate, glycerin laurate, glycerin stearate, glycerin myristate, etc.; $C_{6-30}$ fatty acid esters of $C_{2-8}$ alcohols, especially such waxes as isopropyl myristate, butyl stearate, diisopropyl adipate, diethyl sebacate, etc.; and higher ($C_{6-30}$) fatty acids, especially stearic acid and oleic acid. These oils, fats and fatty acids can be used alone or in admixture.

Preservatives may be incorporated in nasal preparations. Examples of such preservatives include p-hydroxybenzoic acid esters; phenolic compounds such as phenol, cresol, etc.; alcohols such as chlorobutanol, phenylethyl alcohol, propylene glycol, etc.; invert soaps such as benzalkonium chloride, benzethonium chloride, etc.; benzoic acid, sorbic acid, dehydroacetic acid and sulfurous acid and salts thereof; acids and their salts such as sodium hydrogen sulfite.

Oral cavity and oral dosage forms can be produced by the per se conventional procedures. Taking tablets as an example, the desired preparation can be produced by mixing TRH, its salt or its analogue, said hydroxycarboxylic acid or polycarboxylic acid and a lubricating agent into an excipient mixture and, after thorough mixing, compressing the composition into tablets. The excipients which can be used for this purpose include, among others, spray-dried lactose, starch, microcrystalline cellulose, hydroxypropylcellulose, polyvinylpyrrolidone, etc., and the lubricating agent may be selected from among the agents commonly used in the production of tablets, such as stearic acid compounds (e.g. magnesium stearate, calcium stearate, stearic acid, etc.), talc and so on. The quantities and kinds of such excipients and lubricating agents are selected from within those ranges of strength and disintegration characteristics which warrant practically useful tablets.

For example, tablets may be produced by mixing 2 mg of TRH, its salt or its analogue and 1 mg of magnesium stearate into a mixture of 80 mg of spray-dried lactose, 9 mg of starch and 18 mg of microcrystalline cellulose and compression-molding the composition to give 110 mg tablets.

Production of granules may be effected, for example, by charging a mixer with TRH, its salt or its analogue, adding a starch solution prepared by heating a 10% dispersion of corn starch at a suitable temperature, kneading the mixture, drying the same at a suitable temperature in vacuum and milling the dry mixture to give granules.

To produce granules, granular sugar, corn starch, hydroxypropylcellulose (HPC), etc. are admixed with TRH, its salt or its analogue in a mixer and with a 50:50 (v/v) mixture of water and ethyl alcohol being sprayed from a nozzle, the composition is kneaded and granulated, followed by drying in a fluidized bed dryer.

PH of preparations according to this invention is adjusted to 2 to 6. The pH of such preparations is measured as follows. In the case of aqueous preparations such as aqueous solutions, aqueous gels, etc., a single dose unit is added to 10 ml of distilled water and the pH of the solution is measured. In the case of tablets, capsules, granules, granulets, powders and aqueous suppositories, for instance, a single dosage unit is dissolved in 10 ml of distilled water and the pH of the solution is measured. In the case of oil preparations inclusive of oil suppositories, a single dosage unit is added to 10 ml of distilled water, dispersed and dissolved under stirring and centrifuged, and the pH of the aqueous layer is measured at room temperature.

Adjustment of the pH of preparations can be effected by adding an acid, a base, a buffer solution or the like in the course of production of the preparations. As examples of the acid, there may be mentioned inorganic acids (e.g. hydrochloric acid, boric acid, phosphoric acid, carbonic acid, bicarbonic acid, etc.), amino acids and organic acids (e.g. monocarboxylic acids), and the hydroxycarboxylic acids and polycarboxylic acids referred to hereinbefore. The base is exemplified by sodium hydroxide, potassium hydroxide, sodium hydrogen carbonate, sodium carbonate, etc. The buffer solution is exemplified by Sörensen buffer [Ergebniss der Physiology 12, 393(1912)], Clark-Lubs buffer [Journal of Bacteriology 2, (1), 109, 191(1971)], McIlvaine buffer [Journal Biological Chemistry 49, 183(1921)], Michaelis buffer [Die Wasserstoffionenkonzentration, p. 186(1914)], Kolthoff buffer [Biochemische Zeitschrift 179, 410(1926)] and so on.

The dosage of any of the pharmaceutical preparations according to this invention varies with the kind of the active medicament, dosage form, subjects to be treated (e.g. mouse, rat, horse, cattle, man and other warm-blooded mammals) and the object of administration. Taking man as an example, a unit dose as the active medicament is 2 to 20 mg in the case of nasal or rectal administration, and 2 to 40 mg in the case of oral cavity or oral administration.

This invention has the following advantageous features.

(1) A sufficient medical effect can be realized at a low dose level with high efficiency. When it is investigated whether an increased absorption of the drug leads to its increased bioavailability which, in turn, results in an improved antagonistic action to pentobarbital-induced sleep in rats, it is clear that an improved bioavailability leads to an improved efficacy.

(2) It causes little pain at the site of administration and can be used expediently.

(3) For repeated-dose administration, self-administration and, hence, home therapy are feasible.

(4) As TRH, its salt or its analogue is released very gradually from preparations, the blood level and, hence, the clinical efficacy of the drug are sustained for a long time.

The following experimental and working examples are intended to illustrate this invention in further detail. It should be understood that all percents (%) are by weight (w/w %) unless otherwise specified.

EXPERIMENTAL EXAMPLE 1

Male rats of SD strain weighing ca. 300 g, which had been fasted for 24 hours, were dosed with an amount of $^{14}C$-DN-1417 corresponding to 2 mg/kg of DN-1417 by the rectal, nasal, oral cavity and oral routes. The dosage form for nasal, oral cavity or oral administration was either an aqueous solution or an oil solution, and for nasal administration, 0.02 ml of the solution was given with a micropipette; for oral cavity application, a wad of cotton soaked with 0.02 ml of the solution was sublingually administered; and for oral administration, 1 ml of the solution was given by gavage. For rectal administration, 0.1 ml of an aqueous solution was given using a pipette. In the case of a polyethylene glycol suppository and Witepsol W-35 (Dynamit Nobel Chemicals, West Germany) suppository, 50 mg of either suppository was deposited 1.5 cm from the anus.

After administration, 0.2 ml of blood was taken from the cordal vein at timed intervals and the plasma radioactivity was measured with a scintillation counter. Separation of the unmetabolized compound from metabolites was performed by thin-layer electrophoresis. For the evaluation of absorption rates, the area under a curve of the plasma concentration of DN-1417 over a period of 6 hours after administration [AUC (0–6 hr.)] was compared with the corresponding value obtained by subcutaneous administration to calculate the bioavailability of the drug. The results are presented in Table 1.

TABLE 1

Absorption ratio of DN-1417 (2 mg/kg) administered by various routes to rats

| Test material | | AUC (0–6 hr.) μg · ml (n = 3) | | | |
|---|---|---|---|---|---|
| | | Rectal | Nasal | Oral | Subcutaneous |
| Physiological saline | (pH 3.8) | | | | 5.6 |
| Water | (pH 3.8) | 1.4 | 1.2 | 0.5 | |
| 5% Acetic acid | (pH 2.4) | 3.3 | 3.0 | 1.5 | |
| 5% Citric acid | (pH 1.9) | 3.9 | | 1.6 | |
| 5% Lactic acid | (pH 2.0) | 4.7 | | | |
| 5% Gluconic acid | (pH 2.5) | 3.3 | | | |
| 5% l-Malic acid | (pH 1.8) | 4.3 | | 2.0 | |
| 5% dl-Mandelic acid | (pH 2.1) | 6.1 | 3.4 | 3.0 | |
| 2% dl-Tropic acid | (pH 2.3) | 5.1 | | | |
| Witepsol W-35 | | 2.1 | | | |
| 5% dl-Mandelic acid + Witepsol W-35 | | 4.2 | | | |

It will be apparent from Table 1 that, as compared with oral administration, rectal and nasal applications resulted in greater bioavailability and efficient absorption. However, these bioavailabilities are as low as 25% and 21%, respectively, as compared with subcutaneous application and it is clear that an enhancement of absorption is necessary. Keeping the pH of the solutions on the acidic side is, by itself, not sufficient to enhance absorption in any appreciable measure, and the addition of amino acids, lecithin, etc. does not result in any significant improvement of absorption. In contrast, the addition of a hydroxycarboxylic acid results in a remarkable improvement in absorption of DN-1417 and the effect of dl-mandelic acid is especially notable. Absorption from the Witepsol W-35 suppository is also high. While the addition of lower fatty acids such as acetic acid leads to a marked increase of absorption, there is the problem of acetic acid odor. Moreover, local irritations are expected, so that these acids are undesirable in practical use.

EXPERIMENTAL EXAMPLE 2

Using male SD-strain rats weighing ca. 300 g which had been fasted for 24 hours in groups of 3 animals, an amount of $^3H$-TRH equivalent to 2 mg/kg of TRH was administered by the rectal, nasal and oral routes.

The method and volume of administration, the method of collecting blood samples and the method of determination were all the same as described in Experimental Example 1. Evaluation of absorption ratio was made using as a parameter the plasma level of TRH. The results are shown in Table 2.

TABLE 2

| Test material | | AUC (0-2 hr.) μg · hr/ml (n = 3) | | |
|---|---|---|---|---|
| | | Rectal | Nasal | Oral |
| Water | (pH 3.2) | 0.7 | 1.0 | 0.7 |
| 5% dl-Mandelic acid | (pH 2.1) | 2.4 | 2.2 | 1.1 |

It will be apparent from Table 2 that the absorption of TRH from the rectal and nasal mucosa is enhanced by the addition of dl-mandelic acid.

EXPERIMENTAL EXAMPLE 3

Witepsol W-35 suppositories containing 2 mg/kg equivalent of DN-1417 and 5 w/v % of one of the absorption promoting agents mentioned below were rectally administered to groups of 10 male rats of SD strain (4 weeks old) weighing about 80 grams, and the expel ratio of the suppositories and the changes in the epithelium of the local mucous membrane of the rectum after 10 days of administration (once daily) were investigated by scanning electron microscopy.

The results of the expel ratio test using as a control a similar suppository which does not contain any absorption promoting agent are shown in Table 3.

TABLE 3

| Expel ratio of rectal suppositories in rats | | | |
|---|---|---|---|
| | After 10 min. | After 20 min. | After 30 min. |
| Witepsol W-35 suppository | 2/10 | 2/10 | 2/10 |
| Suppository with 5% dl-mandelic acid | 1/10 | 3/10 | 3/10 |
| Suppository with 5% l-malic acid | 1/10 | 3/10 | 3/10 |

N/10: The number of animals which excreted the suppositories per 10 animals.

The scanning electron microscopic findings after 10 consecutive days of administration are not different from those for the control Witepsol W-35 suppository. It is, therefore, apparent that the above acids are not specially irritant to the local mucous membrane of the rectum and are highly safe absorption enhancing agents.

EXAMPLE 1

9.316 Grams of Witepsol W-35 was weighed into a mortar in which it was melted at 40° to 45° C. Then, 500 mg of dl-mandelic acid was added and the mixture was stirred well under warming. Thereafter, 183.6 mg (120 mg as DN-1417) of crystals of DN-1417 citrate were added, followed by thorough stirring. The composition was then poured into a 1-gram suppository mold and cooled gradually to give a 1-gram suppository.

This suppository (one unit) was put in 10 ml of distilled water, melted by warming, and after stirring, was cooled to room temperature. It was then centrifuged and the pH of the water layer was measured with a Horiba H-7Lc pH meter (Horiba Seisakusho Japan). The pH found was 2.6.

EXAMPLE 2

8.906 Grams of Witepsol W-35 was weighed into a mortar in which it was melted by warming at 40°-45° C. Then, 500 mg of dl-mandelic acid and 410 mg of disodium phosphate were added. The mixture was stirred thoroughly under warming. Thereafter, 183.6 mg (120 mg as DN-1417) of crystals of DN-1417 citrate were added, followed by thorough stirring. The resulting composition was poured into a 1-gram suppository mold and cooled gradually to give a 1-gram suppository. This suppository (1 unit) was put in 10 ml of distilled water, melted by warming, and after stirring, was allowed to cool to room temperature. After centrifugation, the pH of the water layer was measured with a Horiba F-7LC pH meter (Horiba Seisakusho Japan). The pH found was 4.1.

EXAMPLE 3

The procedure of Example 1 was repeated under the conditions indicated in Table 4 to produce 1-gram suppositories containing 18.36 mg of DN-1417 citrate.

TABLE 4

| Suppository No. | The kind of acid added | The level of addition of the acid (mg) | pH |
|---|---|---|---|
| 3-1 | Lactic acid | 50 | 2.41 |
| 3-2 | Gluconic acid | 50 | 2.62 |
| 3-3 | Malic acid | 50 | 2.41 |
| 3-4 | Tartaric acid | 50 | 2.46 |
| 3-5 | Citric acid | 50 | 2.50 |
| 3-6 | Salicylic acid | 50 | 2.40 |
| 3-7 | Oxalic acid | 50 | 2.15 |
| 3-8 | Fumaric acid | 50 | 2.4 |
| 3-9 | Maleic acid | 50 | 2.17 |
| 3-10 | Malonic acid | 50 | 2.39 |
| 3-11 | Succinic acid | 50 | 2.74 |
| 3-12 | Glutaric acid | 50 | 2.84 |

EXAMPLE 4

The procedure of Example 2 was repeated under the conditions indicated in Table 5 to produce 1-gram suppositories containing 18.36 mg of DN-1417 citrate.

TABLE 5

| Suppository No. | The kind of acid added | The level of addition of acid (mg) | pH |
|---|---|---|---|
| 4-1 | Lactic acid | 50 | 3.8 |
| 4-2 | Gluconic acid | 50 | 4.4 |
| 4-3 | Malic acid | 50 | 3.8 |
| 4-4 | Tartaric acid | 50 | 3.9 |
| 4-5 | Citric acid | 50 | 4.0 |
| 4-6 | Salicylic acid | 50 | 3.8 |
| 4-7 | Oxalic acid | 50 | 3.6 |
| 4-8 | Fumaric acid | 50 | 3.8 |
| 4-9 | Maleic acid | 50 | 3.6 |
| 4-10 | Malonic acid | 50 | 3.9 |
| 4-11 | Succinic acid | 50 | 4.3 |
| 4-12 | Glutaric acid | 50 | 4.4 |

EXAMPLE 5

9.316 Grams of a mixture of 75 w/w % of polyethylene glycol (PEG) 1000 and 25 w/w % of PEG 4000 was put in a mortar and melted by warming at 50° to 60° C. Then, dl-mandelic acid and DN-1417 citrate were added and the resultant composition was treated as in Example 1 to produce 1-gram suppositories. This preparation (1 unit) was put in 10 ml of distilled water and the pH was measured. The pH found was 2.8.

EXAMPLE 6

8.906 Grams of a mixture of 75 w/w % of polyethylene glycol (PEG) 1000 and 25 w/w % of PEG 4000 was put in a mortar and melted by warming at 50°-60° C. After addition of dl-mandelic acid, disodium phosphate and DN-1417 citrate, the composition was treated in the manner as Example 2 to produce 1-gram suppositories. This preparation (1 unit) was put in 10 ml of distilled water and the pH was measured. The pH found was 4.4.

EXAMPLE 7

In 10 ml of physiological saline were dissolved 500 mg of dl-mandelic acid and 410 mg of disodium phosphate. Then, 367.2 mg of DN-1417 citrate was dissolved to produce a nasal preparation (12 mg/0.5 ml as DN-1417). One dosage unit (0.5 ml) of this preparation was dissolved in 10 ml of distilled water and the pH of the solution was measured. The pH found was 4.0.

EXAMPLE 8

In the manner as Example 7, nasal preparations containing 18.36 mg of DN-1417 citrate were produced under the conditions indicated in Table 6. The single dosage unit of each preparation was 0.5 ml.

TABLE 6

| Preparation No. | The kind of acid added | The level of addition of the acid (mg) | pH |
|---|---|---|---|
| 8-1 | Lactic acid | 25 | 3.8 |
| 8-2 | Gluconic acid | 25 | 4.1 |
| 8-3 | Malic acid | 25 | 4.0 |
| 8-4 | Tartaric acid | 25 | 3.8 |
| 8-5 | Citric acid | 25 | 3.8 |
| 8-6 | Salicylic acid | 25 | 3.8 |
| 8-7 | Oxalic acid | 25 | 3.5 |
| 8-8 | Fumaric acid | 25 | 3.9 |
| 8-9 | Maleic acid | 25 | 3.6 |
| 3-10 | Malonic acid | 25 | 3.8 |
| 3-11 | Succinic acid | 25 | 4.3 |
| 3-12 | Glutaric acid | 25 | 4.3 |

EXAMPLE 9

500 Milligrams of dl-mandelic acid and 410 mg of disodium phosphate were dispersed in 10 ml of Miglyol 812 (Dynamit Nobel, West Germany) under warming at about 40° C. Then, 368.2 mg of DN-1417 citrate was dispersed to produce a nasal preparation (12 mg/0.5 ml as DN-1417). A single dosage unit (0.5 ml) of this preparation was added to 10 ml of distilled water, dispersed under shaking, and centrifuged. The pH of the water layer was 4.1.

The above procedure was repeated except that sesame oil was used in lieu of Miglyol to produce a nasal preparation. The pH of this preparation as measured in the manner as above was 4.1.

EXAMPLE 10

12.5 Milligrams of dl-mandelic acid was milled in a mortar, followed by addition of 176.3 mg of a 3:7 mixture of starch and lactose. After thorough mixing, 61.2 mg of DN-1417 citrate was added. To the mixture was further added 0.75 mg of magnesium stearate and after thorough mixing, the composition was tableted to give tablets for oral/oral cavity administration. One of the tablets was dissolved in 10 ml of distilled water and the pH of the solution was measured. The pH found was 3.2.

EXAMPLE 11

The procedure of Example 10 was repeated under the conditions set forth in Table 7 to produce oral and oral cavity preparations containing 61.2 mg of DN-1417 citrate.

TABLE 7

| Tablet No. | The kind of acid added | The level of addition of the acid (mg) | pH |
|---|---|---|---|
| 11-1 | Lactic acid | 12.5 | 3.02 |
| 11-2 | Gluconic acid | 12.5 | 3.16 |
| 11-3 | Malic acid | 12.5 | 3.10 |
| 11-4 | Tartaric acid | 12.5 | 2.97 |
| 11-5 | Citric acid | 12.5 | 2.99 |
| 11-6 | Salicylic acid | 12.5 | 2.97 |
| 11-7 | Oxalic acid | 12.5 | 2.70 |
| 11-8 | Fumaric acid | 12.5 | 2.98 |
| 11-9 | Maleic acid | 12.5 | 2.75 |
| 11-10 | Malonic acid | 12.5 | 2.94 |
| 11-11 | Succinic acid | 12.5 | 3.33 |
| 11-12 | Glutaric acid | 12.5 | 3.37 |

EXAMPLE 12

The procedure of Example 1 was repeated except that 169.7 mg of TRH tartrate (120 mg as TRH) was used in lieu of 183.6 mg of DN-1417 citrate to produce a suppository. The pH of this preparation as measured in the manner of Example 1 was 2.6.

EXAMPLE 13

The procedure of Example 2 was repeated except that 169.7 mg of TRH tartrate (120 mg as TRH) was used in lieu of 183.6 mg of DN-1417 citrate to produce a suppository. The pH measured in the manner of Example 2 was 4.2.

EXAMPLE 14

In the manner of Example 12, 1-gram suppositories containing 16.97 mg of TRH tartrate (12 mg as TRH) were produced using the following acids indicated in Table 8.

TABLE 8

| Suppository No. | The kind of acid added | The level of addition of the acid (mg) | pH |
|---|---|---|---|
| 14-1 | Lactic acid | 50 | 2.45 |
| 14-2 | Gluconic acid | 50 | 2.65 |
| 14-3 | Malic acid | 50 | 2.53 |
| 14-4 | Tartaric acid | 50 | 2.41 |
| 14-5 | Citric acid | 50 | 2.45 |
| 14-6 | Salicylic acid | 50 | 2.42 |
| 14-7 | Oxalic acid | 50 | 2.18 |
| 14-8 | Fumaric acid | 50 | 2.44 |
| 14-9 | Maleic acid | 50 | 2.20 |
| 14-10 | Malonic acid | 50 | 2.57 |
| 14-11 | Succinic acid | 50 | 2.88 |
| 14-12 | Glutaric acid | 50 | 2.94 |

EXAMPLE 15

In the manner of Example 13, 1-gram suppositories containing 16.97 mg of TRH tartrate (12 mg as TRH) were produced using the acids indicated in Table 9.

TABLE 9

| Suppository No. | The kind of acid added | The level of addition of the acid (mg) | pH |
|---|---|---|---|
| 15-1 | Lactic acid | 50 | 3.9 |
| 15-2 | Gluconic acid | 50 | 4.0 |
| 15-3 | Malic acid | 50 | 4.1 |
| 15-4 | Tartaric acid | 50 | 3.8 |
| 15-5 | Citric acid | 50 | 3.9 |
| 15-6 | Salicylic acid | 50 | 3.8 |
| 15-7 | Oxalic acid | 50 | 3.5 |
| 15-8 | Fumaric acid | 50 | 3.9 |

TABLE 9-continued

| Suppository No. | The kind of acid added | The level of addition of the acid (mg) | pH |
| --- | --- | --- | --- |
| 15-9 | Maleic acid | 50 | 3.4 |
| 15-10 | Malonic acid | 50 | 4.1 |
| 15-11 | Succinic acid | 50 | 4.3 |
| 15-12 | Glutaric acid | 50 | 4.4 |

EXAMPLE 16

The procedure of Example 7 was repeated except that 339.38 mg of TRH tartrate (240 mg as TRH) was used in lieu of 367.2 mg of DN-1417 citrate to produce a nasal preparation (12 mg/0.5 ml as TRH). The pH measured in the manner of Example 1 was 4.1.

EXAMPLE 17

In the manner of Example 16, nasal preparations (0.5 ml per unit) containing 16.97 mg of TRH tartrate were produced using the acids indicated in Table 10.

TABLE 10

| Preparation No. | The kind of acid added | The level of addition of the acid (mg) | pH |
| --- | --- | --- | --- |
| 17-1 | Lactic acid | 25 | 3.8 |
| 17-2 | Gluconic acid | 25 | 4.0 |
| 17-3 | Malic acid | 25 | 4.1 |
| 17-4 | Tartaric acid | 25 | 3.8 |
| 17-5 | Citric acid | 25 | 3.9 |
| 17-6 | Salicylic acid | 25 | 3.9 |
| 17-7 | Oxalic acid | 25 | 3.4 |
| 17-8 | Fumaric acid | 25 | 3.9 |
| 17-9 | Maleic acid | 25 | 3.5 |
| 17-10 | Malonic acid | 25 | 4.2 |
| 17-11 | Succinic acid | 25 | 4.3 |
| 17-12 | Glutaric acid | 25 | 4.4 |

EXAMPLE 18

The procedure of Example 10 was repeated except that 56.56 mg of TRH tartrate (40 mg as TRH) was used in lieu of 61.2 mg of DN-1417 citrate to produce tablets for oral/oral cavity administration. The pH measured in the manner of Example 1 was 3.2.

EXAMPLE 19

In the manner of Example 18, oral and oral cavity tablets containing 56.56 mg of TRH tartrate were produced using the acids indicated in Table 11.

TABLE 11

| Tablet No. | The kind of acid added | The level of addition of the acid (mg) | pH |
| --- | --- | --- | --- |
| 19-1 | Lactic acid | 12.5 | 3.06 |
| 19-2 | Gluconic acid | 12.5 | 3.23 |
| 19-3 | Malic acid | 12.5 | 3.16 |
| 19-4 | Tartaric acid | 12.5 | 3.02 |
| 19-5 | Citric acid | 12.5 | 3.06 |
| 19-6 | Salicylic acid | 12.5 | 3.03 |
| 19-7 | Oxalic acid | 12.5 | 2.70 |
| 19-8 | Fumaric acid | 12.5 | 3.04 |
| 19-9 | Maleic acid | 12.5 | 2.75 |
| 19-10 | Malonic acid | 12.5 | 2.98 |
| 19-11 | Succinic acid | 12.5 | 3.43 |
| 19-12 | Glutaric acid | 12.5 | 3.47 |

What we claim is:

1. A rectal dosage, nasal dosage, oral cavity dosage or oral dosage preparation form, containing
(A) L-pyroglutamyl-L-histidyl-L-prolinamide, its salt, its analogue represented by the formula:

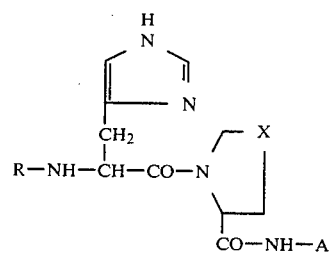

wherein
A is hydrogen, alkyl, aralkyl, alkoxyalkyl, hydroxyalkyl or alkoxy,
R is a group of the formula

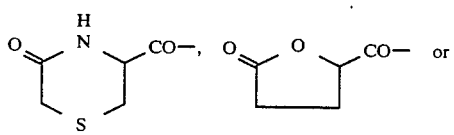

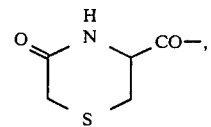

provided that only when A is other than hydrogen may R be

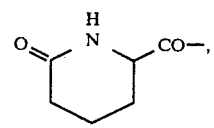

and
X is —CH$_2$—, —CH$_2$CH$_2$— or —S—, or a salt of the analogue, and
(B) at least 1% by weight, based on the weight of the preparation, of an acid selected from the group consisting of a hydroxycarboxylic acid of 2 to 8 carbon atoms, a polycarboxylic acid of 2 to 8 carbon atoms and tropic acid,
said preparation having a pH of 2 to 6.

2. A preparation according to claim 1, wherein the salt is L-pyroglutamyl-L-histidyl-L-prolinamide tartrate.

3. A preparation according to claim 1, wherein the hydroxycarboxylic acid is salicylic acid.

4. A preparation according to claim 1, wherein all the constituents of the analogue are in the form of L-configuration.

5. A preparation according to claim 1, wherein the analogue is γ-butyrolactone-γ-carbonyl-L-histidyl-L-prolinamide.

6. A preparation according to claim 1, wherein the hydroxycarboxylic acid is selected from the group consisting of lactic acid, gluconic acid, malic acid, tartaric acid and citric acid.

7. A preparation according to claim 1, wherein the hydroxycarboxylic acid is mandelic acid.

8. A preparation according to claim 1, wherein the acid is tropic acid.

9. A preparation according to claim 1, wherein the polycarboxylic acid is selected from the group consisting of oxalic acid, fumaric acid, maleic acid, malonic acid, succinic acid and glutaric acid.

10. A preparation according to claim 9, wherein the polycarboxylic acid is succinic acid.

11. A preparation according to claim 1, wherein the acid is selected from the group consisting of lactic acid, gluconic acid, malic acid, citric acid, salicylic acid, mandelic acid, tropic acid, and a polycarboxylic acid of 2 to 8 carbon atoms.

* * * * *